United States Patent [19]

Petzoldt et al.

[11] Patent Number: 5,248,609

[45] Date of Patent: Sep. 28, 1993

[54] RACEMIC SEPARATION OF 7α-ACYLOXY-6β-HYDROXYMETHYL-2-OXABICYCLO[3.3.0]-OCTAN-3-ONES BY STEREOSPECIFIC ENZYMATIC ACYLATE HYDROLYSIS

[75] Inventors: Karl Petzoldt; Helmut Dahl, both of Berlin, Fed. Rep. of Germany

[73] Assignee: Schering Aktiengesellschaft, Berlin and Bergkamen, Fed. Rep. of Germany

[21] Appl. No.: 681,662

[22] PCT Filed: Nov. 12, 1987

[86] PCT No.: PCT/DE87/00520

§ 371 Date: Jul. 13, 1988

§ 102(e) Date: Jul. 13, 1988

[87] PCT Pub. No.: WO88/03570

PCT Pub. Date: May 19, 1988

Related U.S. Application Data

[63] Continuation of Ser. No. 237,111, Jul. 13, 1988, abandoned.

[30] Foreign Application Priority Data

Nov. 13, 1986 [DE]  Fed. Rep. of Germany ....... 3638762

[51] Int. Cl.$^5$ .................. C12P 7/62; C12P 17/04; C12N 9/56
[52] U.S. Cl. .................... 435/280; 435/222; 435/220; 435/196; 435/197; 435/126
[58] Field of Search .............. 435/280, 222, 220, 196, 435/197, 839, 126

[56] References Cited

U.S. PATENT DOCUMENTS 3,963,573  6/1976  Stauffer ............................. 435/280

OTHER PUBLICATIONS

Schutt et al., "Preparation of Optically Active ... ," *Biotech. and Bioeng.* vol. 27, Apr. 1985 pp. 420–433.

Primary Examiner—Irene Marx
Attorney, Agent, or Firm—Millen, White, Zelano, & Branigan

[57] ABSTRACT

The invention relates to a process for the production of optically active (−)-oxabicyclo[3.3.0]octanolones of formula (−)-I

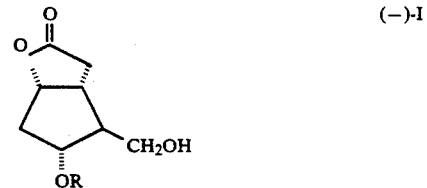

wherein R is defined herein, comprising subjecting a racemic mixture of oxabicyclo[3.3.0]octanolone acylate to stereospecific acylate hydrolysis and separating the resultant products.

11 Claims, No Drawings

RACEMIC SEPARATION OF 7α-ACYLOXY-6β-HYDROXYMETHYL-2-OXABICYCLO[3.3.0]-OCTAN-3-ONES BY STEREOSPECIFIC ENZYMATIC ACYLATE HYDROLYSIS

This application is a continuation of application Ser. No. 07/237,111, filed Jul. 13, 1988, now abandoned.

SUMMARY OF THE INVENTION

The invention relates to a process for the stereospecific acylate hydrolysis of racemic 7α-acyloxy-6β-hydroxymethyl-2-oxabicyclo[3.3.0]octan-3-ones to the corresponding optically active alcohols with the aid of enzymes.

The process is especially suitable for the production of optically active (−)-oxabicyclo[3.3.0]octanolones of Formula (−)-I,

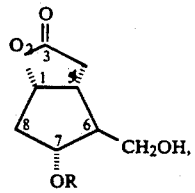

(−)-I wherein R means hydrogen or the residue

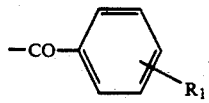

wherein $R_1$ is a hydrogen atom, alkyl of 1–7 carbon atoms, or phenyl.

The process is characterized by enzymatically subjecting racemic oxabicyclo[3.3.0]octanolone acylates of Formula (±)-II

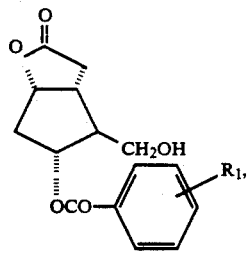

(±)-II wherein $R_1$ has the meanings set forth above, to a stereospecific acylate hydrolysis and separating the (−)-I (R=

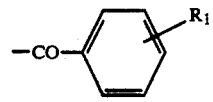

from the saponified (+)-I (R=H) or separating the saponified (−)-I (R=H) from the unsaponified (+)-II.

If $R_1$ represents an alkyl residue of 1–7 carbon atoms, this means the residues methyl, ethyl, n-propyl, isopropyl, n-butyl, isobutyl, sec-butyl, tert-butyl, n-pentyl, isopentyl, sec-pentyl, neopentyl, n-hexyl, isohexyl, n-heptyl, isoheptyl, etc.

The compounds of Formula (−)-I are valuable intermediates in the synthesis of pharmacologically valuable prostaglandin and prostacyclin analogs (overviews, for example, by J. Bindra, R. Bindra, "Prostaglandin Synthesis", Academic Press, New York 1977 and by C. Szantay, L. Novak, "Synthesis of Prostaglandins", Akademiai Kiado, Budapest, 1978).

For the synthesis of the structures analogous to the natural products, the esters of this series of enantiomers are required.

Although asymmetric syntheses are known, the preferred route in industrial production is the introduction of the optical activity by way of a racemic separation at intermediate stage (±)-3. In this connection, the following process steps are necessary:

1. Saponification of the lactone to the hydroxy acid.
2. Conversion into a mixture of diastereomeric salts, e.g., with d-α-phenylethylamine.
3. Crystallization to obtain the diastereomeric pure salt.
4. Conversion of the salt into the optically active lactone (−)-3.
5. Further reaction to the optically active precursor (−)-I.

On account of the tendency displayed by the hydroxy acid of reforming the lactone before optical purification can take place, as well as due to losses in yield during crystallization, the process set out below has not proven satisfactory.

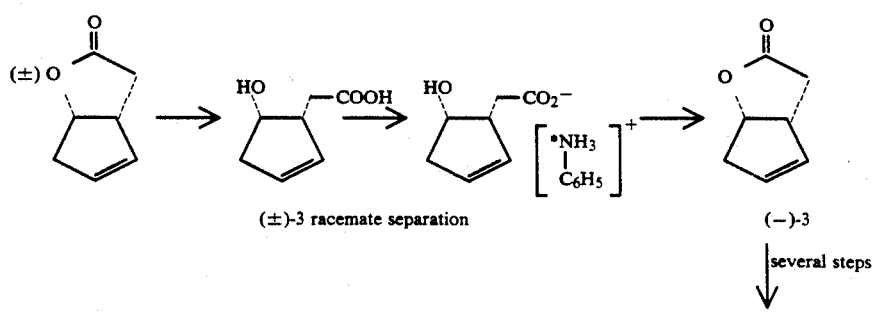

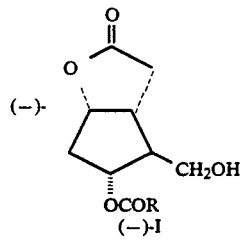

(−)-I

In the present invention, the separation at the stage of the racemic 7α-acyloxy-6β-hydroxymethyl-2-oxabicycl[3.3.0]octan-3-ones of Formula (±)-II is carried out by enzymatic saponification, leading to a product mixture from which the desired compounds of Formula (−)-I can be obtained either by extraction or from the aqueous phase.

The starting compounds can be produced in accordance with British Patent 1,579,464.

The use of the optically active esters of Formula (−)-I (R=

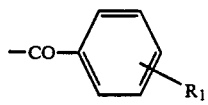

obtained according to the process of this invention as intermediates for the production of pharmacologically valuable prostaglandin and prostacyclin analogs can be derived from the aforementioned overview articles.

The likewise obtainable, optically active diol of Formula (−)-I (R=H) can be utilized, in particular, if, in the subsequent synthesis, the primary hydroxy group must initially be blocked, and the secondary hydroxy group can remain unprotected. This is the case, for example, in the synthesis of carbacyclin intermediates, as described in EP 41 661.

Preferably suited as enzymes for the process of this invention are
subtilisin from *Bacillus subtilis* (company: Boehringer, Mannheim)
lipase "SCLEROTINIA ®" (company: Nagase)
alkaline proteinase (company: Nagase)
protease from *Bacillus subtilis*
"ALCALASE T ®" (company: NOVO)

The enzymes can be utilized in dissolved, suspended or immobilized form (for example on BrCN-activated "SEPHAROSE ®" or on oxirane-acrylic beads, or in some other immobilized form).

The optically active oxabicyclo-octanolone derivatives of Formula (−)-I producible in accordance with the process of this invention are valuable intermediates for the synthesis of pharmacologically effective prostaglandins and prostacyclins. It has been found that the major portion of the stereospecifically hydrolyzing enzymes saponifies the racemic compounds of Formula (±)-II to the optically active diol of Formula (+)-I (R=H), wherein the component of the racemate (±)-II utilized, which corresponds in its absolute configuration to the natural prostacyclin PGJ$_2$, remains unsaponified

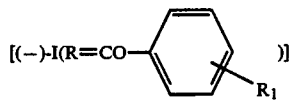

and, after separation from the diol, can be employed for the synthesis of naturally configured prostacyclin analogs.

Other enzymes, in turn, saponify, of the two components of the racemate (±)-II employed, the naturally configured form to the diol (−)-I (R=H) whereas the "false", unnaturally configured enantiomer remains unsaponified. In this case, the diol is utilized for the synthesis of PGJ$_2$-analogous prostacyclins.

The process of this invention otherwise operates under conditions known per se, as conventional for enzymatic reactions. The progression of the enzymatic conversion is controlled by the analysis of continuously withdrawn samples. Suitable analytical methods are HPLC or instant analyses by thin-layer chromatography (silica gel plates by Merck/Darmstadt, development by means of methylene chloride/acetone 1:1 and staining with sulfuric acid).

The reaction is interrupted and the batch is worked up as soon as 50% of the racemic substrate utilized has been converted.

The process of this invention is especially suitable for the stereospecific saponification of the following prostaglandin intermediates:

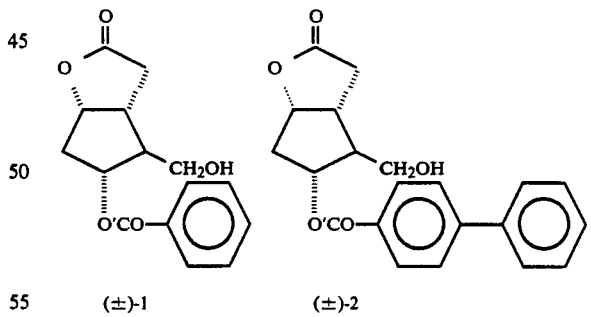

(±)-1        (±)-2

EXAMPLES

The following practical examples serve for explaining the process of this invention.

EXAMPLE 1

300 mg of (±)-7α-benzoyloxy-6β-hydroxymethyl-2-oxabicyclo[3.3.0]octan-3-one is dissolved in 9 ml of ethanol and combined with a solution of 750 mg of alkaline proteinase (company: Nagase) in 100 ml of 0.1-molar phosphate buffer pH 7. The solution is shaken at 28° C. on a rotary shaker, the progression of the reaction being observed for the analysis of continuously taken samples. After 19 hours of reaction time, 50% of the substrate utilized has been converted. The batch is then extracted three times with respectively 50 ml of methyl isobutyl ketone, the unreacted benzoate migrating into the MIBK phase whereas the saponified compound remains in the aqueous phase.

The MIBK extracts are combined and concentrated to dryness under vacuum. The remaining residue is recrystallized from acetone, thus obtaining 135 mg of (−)-7α-benzoyloxy-6β-hydroxymethyl-2-oxabicycl[3.3.0]octan-3-one, mp 116°–117° C., and with a rotation value of $[\alpha]^{20}_D - 80.5°$ (c=1.050 in HCCl₃)

EXAMPLE 2

300 mg of (±)-7α-benzoyloxy-6β-hydroxymerhyl-2-oxabicyclo[3.3.0]octan-3-one is suspended in 100 ml of 0.1-molar phosphate buffer pH 7, 750 mg of subtilisin from Bacillus subtilis (company: Boehringer, Mannheim) is added, and the mixture is homogenized by means of an "Ultra-Turrax" mixer. The suspension is subsequently shaken for 16 hours at 28° C. on a rotary shaker, whereupon 50% of the racemic substrate employed has been saponified. The batch is then concentrated to dryness by means of a water jet aspirator, the remaining residue is eluted three times with methanol, the combined methanol eluates are again concentrated to dryness and chromatographed over a silica gel column (elution mixture methylene chloride-acetone 66+33). The initially eluted fraction 1 contains 122 mg of (−)-7α-benzoyloxy-6β-hydroxymethyl-2-oxabicyclo[3.3.0]octan-3-one, mp 114°–116° C. with a rotation value of $[\alpha]_D - 82.3°$ (c=1.015 in methanol).

EXAMPLE 3

Under the conditions of Example 2, 300 mg of (±)-7α-benzoyloxy-6β-hydroxymethyl-2-oxabicyclo[3.3.0]octan-3-one is treated in phosphate buffer pH 7 with 750 mg of lipase "SCLEROTINA" (company: Nagase) for 64 hours at 28° C. After separating the saponified, unnaturally configured enantiomer by column chromatography, 115 mg of (−)-7α-benzoyloxy-6β-hydroxymethyl-2-oxabicyclo[3.3.0]octan-3-one is obtained, mp 115°–116° with a rotation value of $[\alpha]_D - 79.8°$ (c=1.02 in methanol).

EXAMPLE 4

Under the conditions of Example 2, 300 mg of (±)-7α-benzoyloxy-6β-hydroxymethyl-2-oxabicyclo[3.3.0]octan-3-one is hydrolyzed in phosphate buffer pH 7 with 750 mg of "ALCALASE T" (company: NOVO) for 40 hours at 28° C. After separation of the reaction mixture by means of column chromatography, 142 mg of (−)-7α-benzoyloxy-6β-hydroxymethyl-2-oxabicyclo[3.3.0]octan-3-one is obtained, mp 112°–114° with a rotation value of $[\alpha]_D - 77.1°$ (c=1.005 in methanol).

EXAMPLE 5

Under the conditions of Example 2, 300 mg of (±)-7α-benzoyloxy-6β-hydroxymethyl-2-oxabicyclo[3-.3.0]octan--3-one is treated in phosphate buffer pH 7 with 750 mg of protease from Bacillus subtilis for 15 hours at 28° C. After separation of the reaction mixture by column chromatography, 119 mg of (−)-7α-benzoyloxy-6β-hydroxymethyl-2-oxabicyclo[3.3.0]octan-3-one is obtained, mp 113°–115° C. with a rotation value of $[\alpha]_D - 78.9°$ (c=1.025 in methanol).

We claim:

1. A process for the production of an optically active (−)-oxabicyclo[3.3.0]octanolone of formula (−)-I

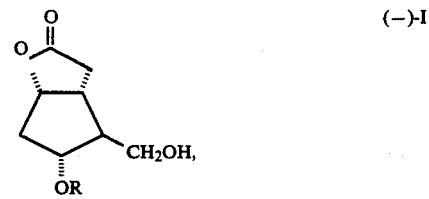

wherein
R is

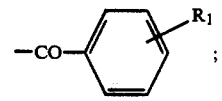

and
R₁ is H, alkyl of 1-7 carbon atoms, or phenyl, comprising the steps of:
 (a) enzymatically subjecting racemic oxabicyclo[3.3.0]octanolone acylate of Formula (±)-II

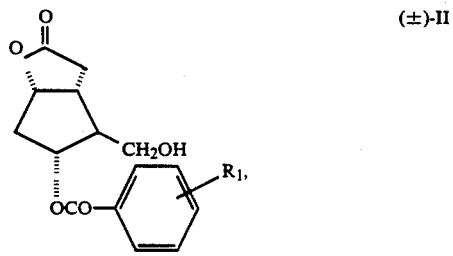

wherein
R₁ in formula II is the same as R₁ is in formula I, to stereospecific acylate hydrolysis using a protease from Bacillus subtilis, wherein (+)-II enantiomer is saponified to (+)-diol; and
 (b) separating said (−)-oxabicyclo[3.3.0]octanolone from the saponified (+)-diol.

2. A process according to claim 1, wherein R₁ is H.

3. A process according to claim 1, wherein R₁ is phenyl.

4. A process according to claim 1, wherein said process consists essentially of step (a) and step (b).

5. A process according to claim 1, wherein said process consists of step (a) and step (b).

6. A process according to claim 1, wherein separation in (b) is provided by extraction.

7. A process according to claim 6, further comprising after separation by extraction, recrystallizing said (−)-oxabicyclo[3.3.0]octanolone.

8. A process for the production of an optically active (−)-oxabicyclo[3.3.0]octanolone of formula (−)-I

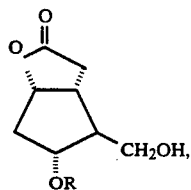
(−)-I wherein
R is

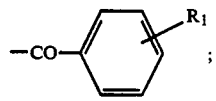
;

and
R₁ is H, alkyl of 1-7 carbon atoms, or phenyl, comprising the steps of:
(a) enzymatically subjecting racemic oxabicyclo[3.3.0]octanolone acylate of Formula (±)-II

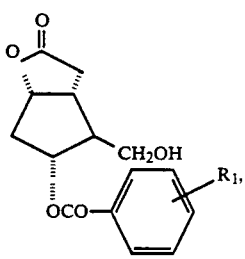
(±)-II wherein
R₁ in formula II is the same as R₁ is in formula I, to stereospecific acylate hydrolysis using a lipase SCLEROTINA, wherein (+)-II enantiomer is saponified to (+)-diol; and
(b) separating said (−)-oxabicyclo[3.3.0]octanolone from the saponified (+)-diol.

9. A process for the production of an optically active (−)-oxabicyclo[3.3.0]octanolone of formula (−)-I

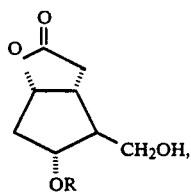
(−)-I wherein
R is

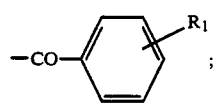
;

and
R₁ is H, alkyl of 1-7 carbon atoms, or phenyl, comprising the steps of:
(a) enzymatically subjecting racemic oxabicyclo[3.3.0]octanolone acylate of Formula (±)-II

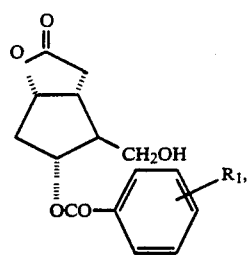
(±)-II wherein
R₁ in formula II is the same as R₁ is in formula I, to stereospecific acylate hydrolysis using subtilisin, wherein (+)-II enantiomer is saponified to (+)-diol; and
(b) separating said (−)-oxabicyclo[3.3.0]octanolone from the saponified (+)-diol.

10. A process for the production of an optically active (−)-oxabicyclo[3.3.0]octanolone of formula (−)-I

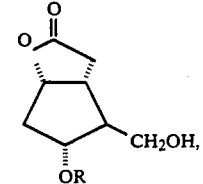
(−)-I wherein
R is

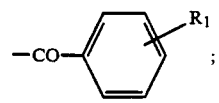
;

and
R₁ is H, alkyl of 1-7 carbon atoms, or phenyl, comprising the steps of:
(a) enzymatically subjecting racemic oxabicyclo[3.3.0]octanolone acylate of Formula (±)-II

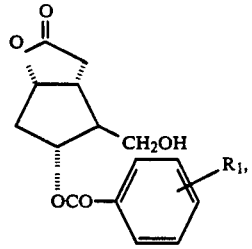
(±)-II wherein
R₁ in formula II is the same as R₁ is in formula I, to stereospecific acylate hydrolysis using ALCALASE T ®, wherein (+)-II enantiomer is saponified to (+)-diol; and
(b) separating said (−)-oxabicyclo[3.3.0]octanolone from the saponified (+)-diol.

11. A process for the production of an optically active (−)-oxabicyclo[3.3.0]octanolone of formula (−)-I

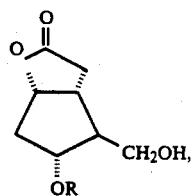 (−)-I wherein
R is

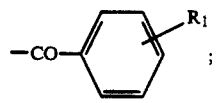 ;

and
$R_1$ is H, alkyl of 1–7 carbon atoms, or phenyl, comprising the steps of:

(a) enzymatically subjecting racemic oxabicyclo[3.3.0]octanolone acylate of Formula (±)-II

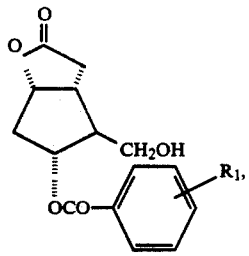 (±)-II wherein
$R_1$ in formula II is the same as $R_1$ is in formula I, to sterospecific acylate hydrolysis using alkaline proteinase from Nagase, wherein (+)-(II) enantiomer is saponified to (+)-diol; and (b) separating said (−)-oxabicyclo[3.3.0]octanolone from the saponified (+)-diol.

* * * * *